(12) United States Patent
Sugita

(10) Patent No.: US 8,414,574 B2
(45) Date of Patent: Apr. 9, 2013

(54) TREATMENT INSTRUMENT HAVING A FRONT-END TREATMENT MEMBER

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 1472 days.

(21) Appl. No.: 11/755,182

(22) Filed: May 30, 2007

(65) Prior Publication Data

US 2007/0282326 A1    Dec. 6, 2007

(30) Foreign Application Priority Data

Jun. 1, 2006   (JP) .................. 2006-152950
Jun. 22, 2006  (JP) .................. 2006-172259

(51) Int. Cl.
  *A61B 18/14*    (2006.01)
(52) U.S. Cl. ........................................ 606/41
(58) Field of Classification Search .............. 606/41
  See application file for complete search history.

(56) References Cited

U.S. PATENT DOCUMENTS

| | | | | |
|---|---|---|---|---|
| 5,647,870 A | * | 7/1997 | Kordis et al. .................. | 606/41 |
| 2003/0216721 A1 | * | 11/2003 | Diederich et al. ............... | 606/28 |
| 2004/0172018 A1 | * | 9/2004 | Okada ............................. | 606/46 |
| 2005/0215853 A1 | | 9/2005 | Ouchi | |
| 2006/0178656 A1 | | 8/2006 | Sugita et al. | |
| 2006/0178657 A1 | | 8/2006 | Sugita et al. | |

FOREIGN PATENT DOCUMENTS

| | | |
|---|---|---|
| JP | 5-253297 | 10/1993 |
| JP | 6-304132 | 11/1994 |
| JP | 9-84874 | 3/1997 |
| JP | 2002 113016 | 4/2002 |
| JP | 2005-152504 | 6/2005 |
| JP | 2005 270240 | 10/2005 |
| JP | 2005-270240 | 10/2005 |
| JP | 2005 279126 | 10/2005 |

OTHER PUBLICATIONS

English language Abstract of JP 2002-113016.

* cited by examiner

*Primary Examiner* — Michael Peffley
*Assistant Examiner* — Daniel Fowler
(74) *Attorney, Agent, or Firm* — Greenblum & Bernstein P.L.C.

(57) ABSTRACT

There is provided a treatment instrument, which is provided with a flexible sheath configured such that at least a part thereof is formed of a flexible tube, an operation wire inserted into the flexible sheath to be movable in an axial direction of the flexible sheath, a front-end treatment member connected to a leading end of the operation wire so that the front-end treatment member is allowed to protrude from a front end of the flexible sheath and retracts into the front end of the flexible sheath in accordance with movement of the operation wire, and an at least one elastic member that has elasticity and is located in a front end portion of the flexible sheath in a condition where the at least one elastic member is elastically deformed between an inner surface of the flexible sheath and an outer circumferential surface of the operation wire.

29 Claims, 17 Drawing Sheets

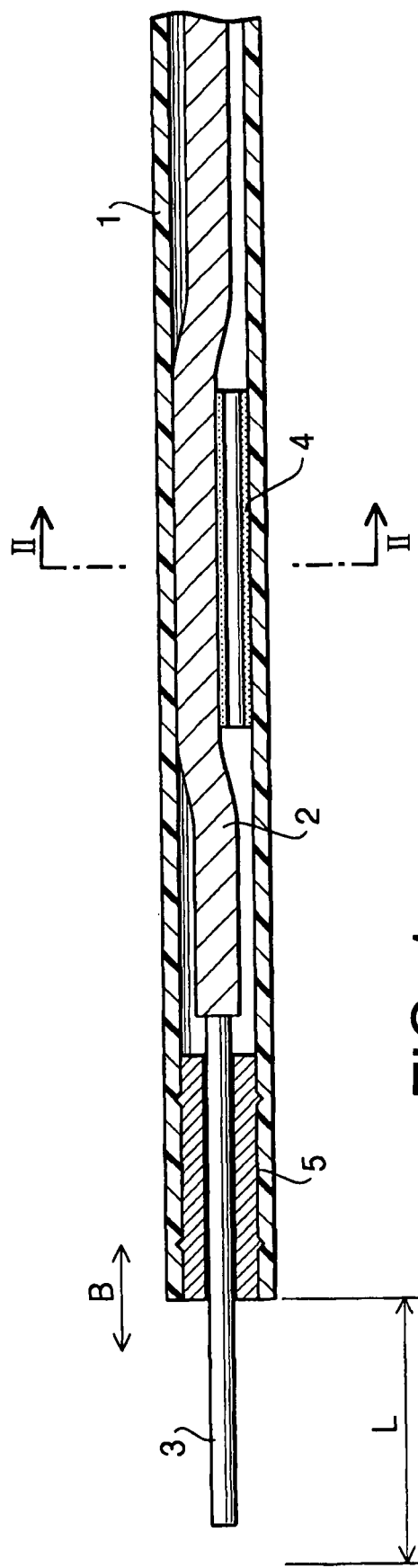
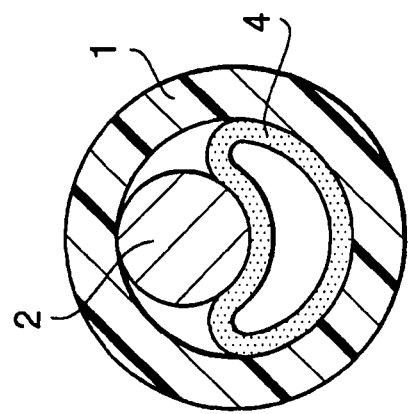
FIG. 1
FIG. 2

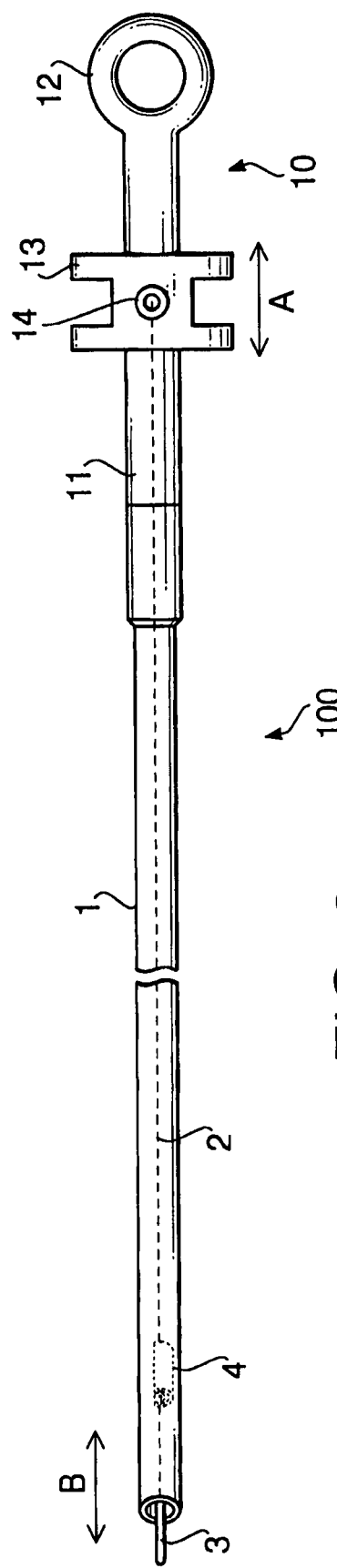
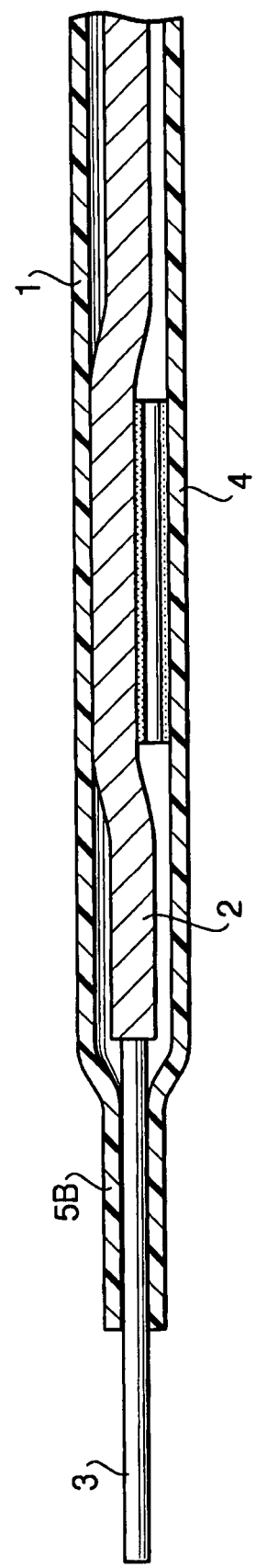
FIG. 3
FIG. 4

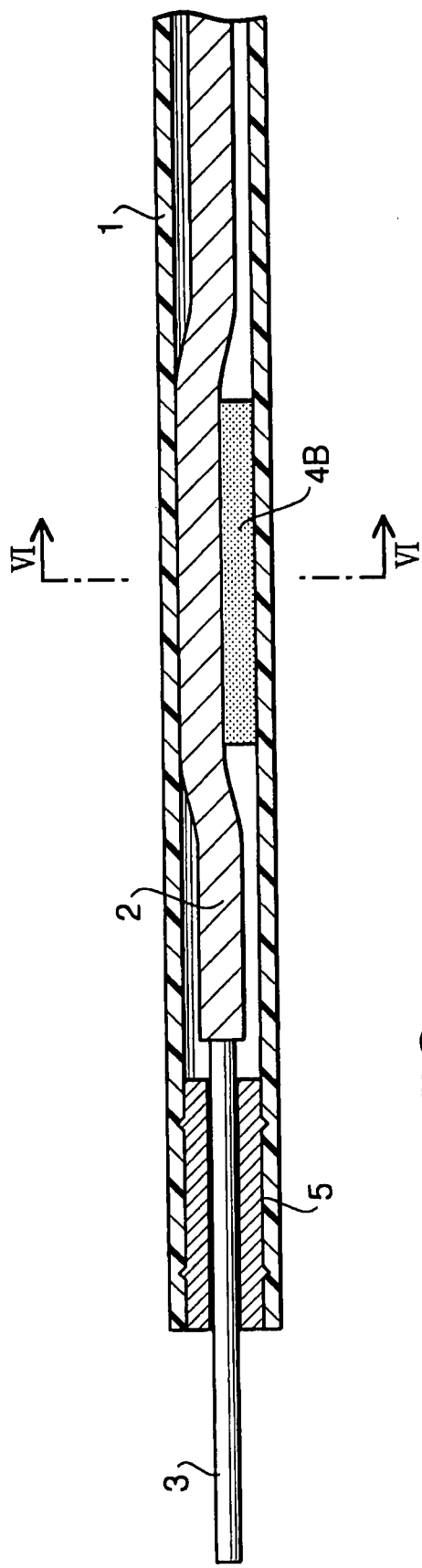
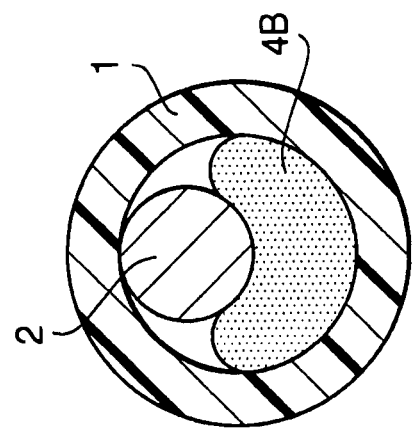
FIG. 5
FIG. 6

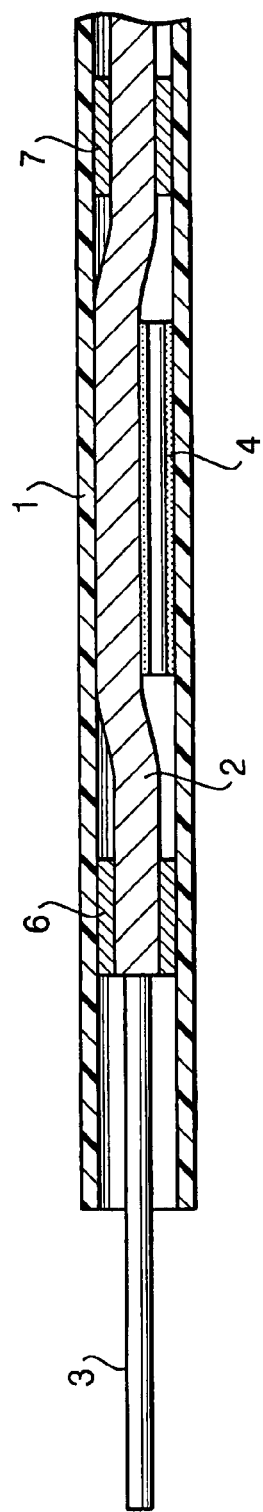
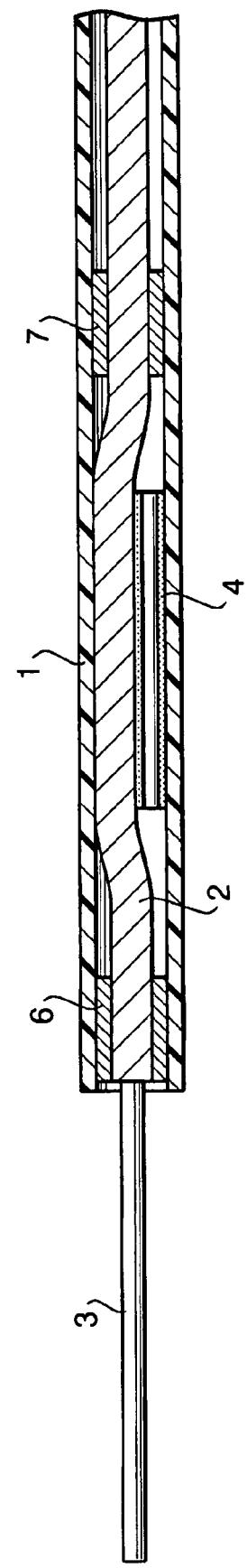
FIG. 10
FIG. 11

TREATMENT INSTRUMENT HAVING A FRONT-END TREATMENT MEMBER

BACKGROUND OF THE INVENTION

The present invention relates to a retractable treatment instrument to be inserted into an instrument-inserting channel of an endoscope.

In general, the treatment instrument includes a front-end treatment member connected to a leading end of an operation wire inserted into a flexible sheath to be movable along an axial direction of the flexible sheath. The front-end treatment member is capable of protruding from a front end of the flexible sheath and retracting into the flexible sheath. It is also possible to adjust a projected length of the front-end treatment member from the front end of the flexible sheath by moving the operation wire in the axial direction. Examples of such a treatment instrument are disclosed in Japanese Patent Provisional Publications No. 2002-113016 (hereafter, referred to as JP 2002-113016A) and No. 2005-270240 (hereafter, referred to as JP 2005-270240A).

The retractable treatment instrument disclosed in JP 2002-113016A is provided with a screw member at the front end of the flexible sheath so that the screw member is used to adjust the projected length of the front-end treatment member from the front end of the flexible sheath. According to the retractable treatment instrument disclosed in JP 2005-270240A, the front-end treatment member is configured to have a wide part at its proximal portion. The width of the wide part of the front-end treatment member is larger than an inner diameter of a flexible tube (flexible sheath) so that the projected length of the front-end treatment member from the leading end of the flexible tube can be kept at an adjusted position by friction between an edge of the wide part and the inner surface of the flexible tube.

According to the configuration disclosed in each of JP 2002-113016A and JP 2005-270240A, the projected length of the front-end treatment member can be adjusted at a desired length. Further, since the front-end treatment member can be fixed stably at the adjusted position, the projected length of the front-end treatment member is not changed by a force applied to the front-end treatment member when the front-end treatment member touches tissue of a body cavity during a diagnostic operation.

However, the treatment instrument disclosed in JP 2002-113016A has a drawback that the structure of the treatment instrument becomes inevitably complicated if the requirement for providing the screw member at the front end of the flexible sheath is achieved. In general, providing a screw member at the front end of the flexible sheath of the treatment instrument whose diameter is approximately 2 mm makes it impractical to use the treatment instrument for endoscopes. In addition, it is impossible to adjust the projected length of the front-end treatment member while the front portion of the treatment instrument is in the body cavity. Therefore, it is necessary to withdraw the treatment instrument from the instrument-inserting channel of the endoscope to adjust the projected length of the front-end treatment member.

The treatment instrument disclosed in JP 2005-270240A has a drawback that the manufacturing cost of the front-end treatment member is relatively high because it is necessary to form the wide part at the proximal portion of the front-end treatment member. In addition, there is a possibility that friction between the edge of the wide part and the inner surface of the flexible tube decreases considerably due to permanent deformation of the cross-sectional shape of the flexible tube caused in the direction in which the inner surface of the flexible tube is elongated by the wide part of the front-end treatment member. If the friction decreases as mentioned above, it becomes difficult to keep the projected length of the front-end treatment member at the desired length stably.

SUMMARY OF THE INVENTION

The present invention is advantageous in that it provides a treatment instrument for endoscopes configured to be able to keep a projected length of a front-end treatment member at a desired length stably and to be manufactured at low cost, while achieving high practicability.

According to an aspect of the invention, there is provided a treatment instrument for endoscopes. The treatment instrument is provided with a flexible sheath configured such that at least a part thereof is formed of a flexible tube, an operation wire inserted into the flexible sheath to be movable in an axial direction of the flexible sheath, a front-end treatment member connected to a leading end of the operation wire so that the front-end treatment member is allowed to protrude from a front end of the flexible sheath and retracts into the front end of the flexible sheath in accordance with movement of the operation wire, and an at least one elastic member that has elasticity and is located in a front end portion of the flexible sheath in a condition where the at least one elastic member is elastically deformed between an inner surface of the flexible sheath and an outer circumferential surface of the operation wire.

According to the above mentioned configuration, it is possible to keep the projected length of the front-end treatment member from the front end of the flexible sheath at a desired length stably over a long time. It should be noted that such advantages are achieved in a low cost while achieving excellent practicability.

In at least one aspect, friction caused among the flexible sheath, the operation wire and the at least one elastic member is applied to movement of the operation wire in the axial direction. In this case, a projected length of the front-end treatment member from the front end of the flexible sheath can be adjusted by moving the operation wire in the axial direction.

In at least one aspect, the front-end treatment member is a high frequency electrode. The operation wire has conductivity and is electrically continuous with the front-end treatment member.

In at least one aspect, the operation wire is formed by twisting a plurality of wires. In this case, the front-end treatment member is formed by elongating one of the plurality of wires forming the operation wire.

In at least one aspect, the at least one elastic member is located in the front end portion of the flexible sheath without being fixed to an inner surface of the flexible sheath.

In at least one aspect, the at least one elastic member is a tube-like member.

In at least one aspect, the at least one elastic member is a tube-like member having an outer diameter smaller than an inner diameter of the flexible sheath.

In at least one aspect, the at least one elastic member is a solid rod-like member.

In at least one aspect, the at least one elastic member is a ring-shaped member located in the front end portion of the flexible sheath to surround the operation wire.

In at least one aspect, the treatment instrument is further provided with a front stopper located in the flexible sheath to prevent the at least one elastic member from being detached from the front end of the flexible sheath.

In at least one aspect, the front stopper is located at the front end of the flexible sheath.

In at least one aspect, the front stopper is fixed to the front end of the flexible sheath.

In at least one aspect, the front stopper is formed by narrowing the front end of the flexible sheath.

In at least one aspect, the front stopper is attached to the operation wire.

In at least one aspect, the front stopper is a pipe-like member having an outer diameter smaller than an inner diameter of the flexible sheath.

In at least one aspect, the front stopper is attached to the operation wire such that the front stopper does not protrude from the front end of the flexible sheath when the operation wire moves to a front end point in a moving range of the operation wire which is allowed to move in the axial direction within the moving range.

In at least one aspect, the treatment instrument is further provided with a rear stopper located in the flexible sheath to restrict movement of the at least one elastic member toward a rear side.

In at least one aspect, the rear stopper is attached to the operation wire.

In at least one aspect, the rear stopper is a pipe-like member having an outer diameter smaller than an inner diameter of the flexible sheath.

In at least one aspect, the at least one elastic member has an area to which a surface treatment is applied to increase friction caused between the inner surface of the flexible sheath and the area, the area facing the inner surface of the flexible sheath and not facing the outer circumferential surface of the operation wire.

In at least one aspect, the at least one elastic member comprises a plurality of elastic members each of which has elasticity and is located in the front end portion of the flexible sheath in the condition where the each of the plurality of elastic members is elastically deformed between the inner surface of the flexible sheath and the outer circumferential surface of the operation wire.

In at least one aspect, the at least one elastic member is located in the flexible sheath by pressing the at least one elastic member into the front end portion of the flexible sheath.

In at least one aspect, the treatment instrument further includes an operation unit that is provided at a proximal end portion of the flexible sheath and is connected to a proximal end of the operation wire so that the operation wire is rotated about an axis line of the operation wire by operating the operation unit. In this configuration, at least a front end portion of the operation wire is a twisted wire formed by twisting a plurality of wires. The front-end treatment member moves along the axis line when rotated about the axis line by rotation of the operation wire, due to a condition where the front end portion of the operation wire is pressed against the elastic member. Further, a projected length of the front-end treatment member from the front end of the flexible sheath can be adjusted by rotating the operation wire using the operation unit.

With this configuration, it is possible to adjust the projected length of the front-end treatment member to a desired length in a condition where the treatment instrument is inserted in a treatment-inserting channel of an endoscope. It should be noted that such advantages are achieved in a low cost while achieving excellent practicability.

In at least one aspect, an entire part of the operation wire is formed by twisting a plurality of wires.

In at least one aspect, the operation wire has a first twisted wire part and a second twisted wire part which have twisting pitches different from each other and which are connected with each other in series. The first twisted wire part is situated at the front end portion of the operation wire to be pressed against the elastic member. Further, the second twisted wire part is located on a rear side with respect to the first twisted wire part.

In at least one aspect, the twisting pitch of the first twisted wire part is larger than that of the second twisted wire part.

In at least one aspect, the second twisted wire part is formed of a torque wire.

In at least one aspect, the treatment instrument further includes a position restriction member located in the flexible sheath to restrict movement of the elastic member. In this case the position restriction member prevents the elastic member from moving to a position at which the front end portion of the operation wire does not engage with the elastic member.

In at least one aspect, the position restriction member is located at the front end of the flexible sheath.

In at least one aspect, the position restriction member is formed by deforming the front end of the flexible sheath.

In at least one aspect, the position restriction member includes an area which is a part of a surface of the elastic member and has been subjected to a surface treatment. In this case, the area contacts the inner surface of the flexible sheath and does not contact the outer circumferential surface of the operation wire.

In at least one aspect, the position restriction member is attached to the operation wire.

In at least one aspect, the operation wire includes a first operation unit configured to rotate the operation wire about the axis line, and a second operation unit configured to move the operation wire in the axis direction.

According to another aspect of the invention, there is provided a treatment instrument for endoscopes. The treatment instrument is provided with a flexible sheath configured such that at least a part thereof is formed of a flexible tube, an operation wire inserted into the flexible sheath to be movable in an axial direction of the flexible sheath, an operation unit that is provided at a proximal end portion of the flexible sheath and is connected to a proximal end of the operation wire so that the operation wire is rotated about an axis line of the operation wire by operating the operation unit, a front-end treatment member connected to a leading end of the operation wire, and an at least one elastic member that has elasticity and is located in a front end portion of the flexible sheath in a condition where the at least one elastic member is elastically deformed between an inner surface of the flexible sheath and an outer circumferential surface of the operation wire.

In this configuration, at least a front end portion of the operation wire is a twisted wire formed by twisting a plurality of wires. The front-end treatment member moves along the axis line when rotated about the axis line by rotation of the operation wire, due to a condition where the front end portion of the operation wire is pressed against the elastic member. Further, a projected length of the front-end treatment member from the front end of the flexible sheath can be adjusted by rotating the operation wire using the operation unit.

With this configuration, it is possible to adjust the projected length of the front-end treatment member to a desired length in a condition where the treatment instrument is inserted in a treatment-inserting channel of an endoscope. It should be noted that such advantages are achieved in a low cost while achieving excellent practicability.

BRIEF DESCRIPTION OF THE ACCOMPANYING DRAWINGS

FIG. 1 is a side cross section of a treatment instrument according to a first embodiment, illustrating a structure of a front end portion of a flexible sheath.

FIG. 2 is a cross sectional view of the treatment instrument along a line II-II in FIG. 1.

FIG. 3 illustrates the entire configuration of a treatment instrument for endoscopes according to a first embodiment of the invention.

FIG. 4 is a side cross section of a front end portion of a flexible sheath according to a second embodiment.

FIG. 5 is a side cross section of a front end portion of a flexible sheath according to a third embodiment.

FIG. 6 is a cross sectional view of the flexible sheath along a line VI-VI in FIG. 5.

FIG. 10 is a side cross section of a front end portion of a flexible sheath according to a fifth embodiment.

FIG. 11 illustrates a situation where an operation wire is fully inserted toward the front side.

DETAILED DESCRIPTION OF THE EMBODIMENTS

Figure 7:
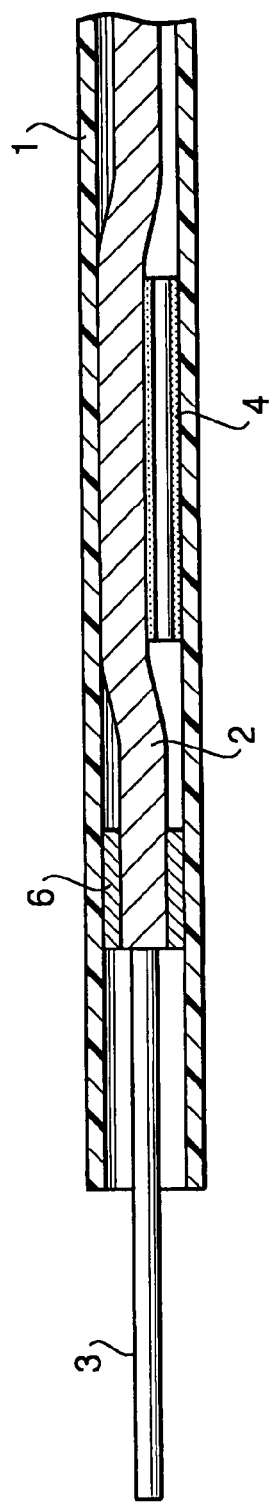
FIG. 7 is a side cross section of a front end portion of a flexible sheath according to a fourth embodiment.

Hereinafter, embodiments according to the invention are described with reference to the accompanying drawings.

First Embodiment

FIG. 3 illustrates the entire configuration of a treatment instrument 100 for endoscopes according to a first embodiment of the invention. The treatment instrument 100 has a flexible sheath 1 formed of a flexible tube such as a tetrafluoroethylene resin tube, and an operation wire 2 formed of a twisted wire of stainless steel wires having conductivity. The operation wire 2 is elongated in the axial direction along the length of the treatment instrument 100 to be movable in the axial direction. The treatment instrument 100 is inserted into an instrument-inserting channel of an endoscope.

A front-end treatment member 3 is provided at the front end of the flexible sheath 1. The front-end treatment member 3 is a thin straight rod-like member having conductivity to function as a high-frequency electrode. The front-end treatment member 3 is connected to a leading end of the operation wire 2 so that the front-end treatment member 3 is able to protrude from the front end of the flexible sheath 1 and to retract into the front end of the flexible sheath 1 in accordance with the movement of the operation wire 2.

The treatment instrument 100 includes an operation unit 10. The operation unit 10 includes a fixed hook 12 formed at the rear of an operation body 11 connected to the proximal end of the flexible sheath 1, and a movable hook 13 mounted on the operation body 11 to be slidable along the operation body 11 in the axial direction. The movable hook 13 is connected to the proximal end of the operation wire 2. A terminal 14 is provided on the movable hook 13 so that when a high frequency power supply cable is connected to the terminal 14, the high frequency voltage is supplied to the front-end treatment member 3 through the terminal 14 and the operation wire 2.

According to the above mentioned structure, when the movable hook 13 slides along the operation body 11 as shown by an arrow A in FIG. 3, the operation wire 2 moves in the axial direction in the flexible sheath 1 and the front-end treatment member 3 also moves along the axial direction at the front end portion of the flexible sheath 1 as shown by an arrow B in FIG. 3. By this structure, it is possible to adjust a projected length of the front-end treatment member 3 from the front end of the flexible sheath 1.

As shown in FIG. 3, the treatment instrument 100 is further provided with a flexible friction producing member 4 at the front end portion of the flexible sheath 1. The flexible friction producing member 4 serves to keep the projected length of the front-end treatment member 3 at a desired length stably.

FIG. 1 is a side cross section of the treatment instrument 100, illustrating a structure of the front end portion of the flexible sheath 1. The operation wire 2 is a twisted wire formed by twisting more than one wire. The front-end treatment member 3 is formed by elongating one of the wires (e.g., a core wire) forming the operation wire 2 in the axial direction so that the front-end treatment member 3 is seamlessly connected to the operation wire 2.

FIG. 2 is a cross sectional view of the treatment instrument 100 along a line II-II in FIG. 1. The flexible friction producing member 4 is a flexible tube-like member. As shown in FIG. 1, the flexible friction producing member 4 is pressed into the front end portion of the flexible sheath 1 so that, in the state shown in FIG. 2, the flexible friction producing member 4 is pressed by an outer circumferential surface of the operation wire 2 and an inner surface of the flexible sheath 1 and that the flexible friction producing member 4 has a recessed portion where the flexible friction producing member 4 is elastically deformed by the outer circumferential surface of the operation wire 2.

Since the flexible friction producing member 4 is simply pressed into the flexible sheath 1, the flexible friction producing member 4 is not fixed with respect to the flexible sheath 1. Such a configuration contributes to reducing the manufacturing cost of the treatment instrument 100.

For example, the flexible friction producing member 4 is formed of a tetrafluoroethylene resin tube which has an outer diameter smaller than the inner diameter of the flexible sheath 1 and has a thickness smaller than that of the flexible sheath 1. Although the material (i.e., the tetrafluoroethylene resin tube) does not have great elasticity, the recessed portion (where the tetrafluoroethylene resin tube is elastically deformed) exhibits a strong force of resilience for restoring the recessed portion to its original shape (i.e., a cylindrical shape). Such a strong force of resilience acts on the operation wire 2 and the flexible sheath 1.

A contact area where the flexible friction producing member 4 contacts the inner surface of the flexible sheath 1 is larger than a contact area where the flexible friction producing member 4 contacts the outer circumferential surface of the operation wire 2. Therefore, when the operation wire 2 moves in the axial direction in the flexible sheath 1, only the operation wire 2 moves in the axial direction and the flexible friction producing member 4 does not move in the axial direction as long as the flexible friction producing member 4 is not hooked onto the operation wire 2. Consequently, when the operation wire 2 moves in the axial direction in the flexible sheath 1, friction caused between the operation wire 2 and the flexible friction producing member 4 and friction caused between the operation wire 2 and the inner surface of the flexible sheath 1 act on the movement of the operation wire 2.

There is a possibility that the flexible friction producing member 4 is hooked onto the operation wire 2 and the flexible friction producing member 4 also moves in the flexible sheath 1 according to the movement of the operation wire 2. In this case, friction caused between the inner surface of the flexible sheath 1 and the operation wire 2 and friction caused between the flexible friction producing member 4 and the inner surface of the flexible sheath 1 act on the movement of the operation wire 2.

The friction acting on the movement of the operation wire 2 in the axial direction is proportional to the force of resilience caused in the recessed portion of the flexible friction producing member 4 to restore the recessed shape to its original shape. Such a configuration makes an operation of the movable hook 13 to move the operation wire 2 feel slippery while also giving feeling of resistance to the operation of the movable hook 13 to some extent. In other words, the movable hook 13 shows such a feeling that the operation wire 2 is pressed against a smooth surface of the tetrafluoroethylene resin tube.

According to the above mentioned configuration, it is possible to adjust the projected length of the front-end treatment member 3 within the length L shown in FIG. 1. That is, the operator is able to adjust the projected length of the front-end treatment member 3 to a desired length according to the intended purpose of the treatment instrument 100. As described above, the projected length of the front-end treatment member 3 is stably maintained. Therefore, the projected length is not changed by such an external force that is caused when the front-end treatment member 3 touches tissue of a body cavity during a diagnostic operation because the friction is applied to the operation wire 2 by the flexible friction producing member 4.

In this embodiment, the treatment instrument 100 is configured such that the tip end of the front-end treatment member 3 fully retracts into the front end portion of the flexible sheath 1 (i.e., the tip end of the front-end treatment member 3 does not project from the front end of the flexible sheath 1) when the operation wire 2 (i.e., the movable hook 13) is fully withdrawn to the rear side. However, the tip end of the front-end treatment member 3 may slightly protrude from the front end of the flexible sheath 1 when the movable hook 13 is fully withdrawn.

The strength of friction acting on the movement of the operation wire 2 is substantially proportional to the length of the flexible friction producing member 4. Therefore, the strength of friction acting on the movement of the operation wire 2 can be adjusted to a desirable strength by determining the length of the flexible friction producing member 4 in the manufacturing process, according to the intended purpose of the treatment instrument 100 or required specifications of the treatment instrument 100. According to the embodiment, it is also possible to replace the flexible friction producing member 4 with a new one because the flexible friction producing member 4 is not fixed to the inner surface of the flexible sheath 1.

As shown in FIG. 1, a stopper 5 may be provided at the front end of the flexible sheath 1 so as to prevent the flexible friction producing member 4 from being detached from the front end of the flexible sheath 1. The stopper 5 is, for example, a rod-like member made of PEEK (Poly-ether-ether-keton) resin, and may be pressed into the flexible sheath 1. The stopper 5 has a through hole formed therein along the axial direction so that the front-end treatment member 3 smoothly penetrates the through hole.

According to the above mentioned structure, the front-end treatment member 3 is able to protrude from the front end of the flexible sheath 1 along the axial direction. The movement of the front-end treatment member 3 toward the front side is stopped when the front edge of the operation wire 2 touches the rear end of the stopper 5. That is, the maximum projected length of the front-end treatment member 3 is limited by the rear end of the stopper 5.

Even if the flexible friction producing member 4 moves toward the front end of the flexible sheath 1 while being pulled by the operation wire 2, the movement of the flexible friction producing member 4 is stopped when the flexible friction producing member 4 touches the rear end of the stopper 5. That is, the flexible friction producing member 4 is prevented from being detached from the front end of the flexible sheath 1 by the rear end of the stopper 5.

Second Embodiment

Hereafter, a treatment instrument according to a second embodiment is described. Since the second embodiment corresponds to a variation of the first embodiment, in the following, only the feature of the second embodiment is explained. In the drawings for the second embodiment, to elements which are substantially the same as those of the first embodiment, the same reference numbers are assigned and explanations thereof will not be repeated.

FIG. 4 is a side cross section of the front end portion of the flexible sheath 1 according to the second embodiment. In this embodiment, a narrowed portion 5B is formed at the front end of the flexible sheath 1 in place of providing a separate stopper (the stopper 5) in the front end of the flexible sheath 1. For example, the narrowed portion 5B can be formed by narrowing the diameter of the front end of the flexible sheath 1 by thermoforming.

Third Embodiment

Hereafter, a treatment instrument according to a third embodiment is described. Since the third embodiment corresponds to a variation of the first embodiment, in the following, only the feature of the third embodiment is explained. In the drawings for the third embodiment, to elements which are substantially the same as those of the first embodiment, the same reference numbers are assigned and explanations thereof will not be repeated.

FIG. 5 is a side cross section of the front end portion of the flexible sheath 1 according to the third embodiment. FIG. 6 is a cross sectional view of the flexible sheath 1 along a line VI-VI in FIG. 5. In this embodiment, a solid rod-like member having elasticity (a flexible friction producing member 4B) is used to achieve the same functions as those achieved by the flexible friction producing member 4 according to the first embodiment. For example, the flexible friction producing member 4B is made of silicon resin or silicon rubber.

Fourth Embodiment

Hereafter, a treatment instrument according to a fourth embodiment is described. Since the fourth embodiment corresponds to a variation of the first embodiment, in the following, only the feature of the fourth embodiment is explained. In the drawings for the fourth embodiment, to elements which are substantially the same as those of the first embodiment, the same reference numbers are assigned and explanations thereof will not be repeated.

FIG. 7 is a side cross section of the front end portion of the flexible sheath 1 according to the fourth embodiment. In this embodiment, a front side stopper 6 is provided in the flexible sheath 1 in place of the stopper 5. Similarly to the stopper 5, the front side stopper 6 serves to prevent the flexible friction producing member 4 from being detached from the front end of the flexible sheath 1. The front side stopper 6 is a pipe-like member and is attached to the leading end of the operation wire 2. For example, the front side stopper 6 is made of metal or rigid plastic. The front side stopper 6 has an outer diameter smaller than the inner diameter of the flexible sheath 1 and is fixed to the leading end of the operation wire 2, for example, by soldering, adhesive joining, or swaging.

Figure 8:
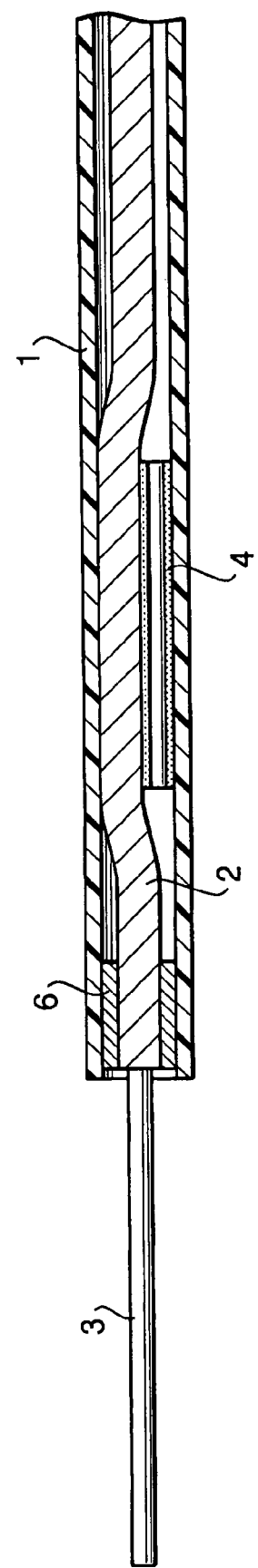
FIG. 8 illustrates a situation where an operation wire is fully inserted toward the front side.

FIG. 8 illustrates a situation where the operation wire 8 is fully inserted toward the front side. The length of the operation wire 2 is adjusted such that the front side stopper 6 does not protrude from the front end of the flexible sheath 1 when the operation wire 2 is fully inserted toward the front side. Therefore, the flexible friction producing member 4 is prevented from being detached from the front end of the flexible sheath 1 because even if the flexible friction producing member 4 moves toward the front end of the flexible sheath 1, the movement of the flexible friction producing member 4 toward the front side is stopped by the front side stopper 6.

Figure 9:
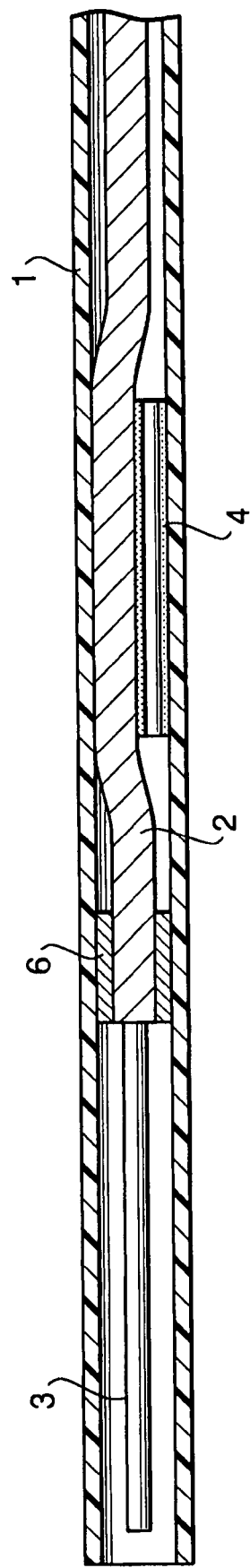
FIG. 9 illustrates a situation where the operation wire is fully withdrawn toward the rear side.

FIG. 9 illustrates a situation where the operation wire 2 is fully withdrawn toward the rear side. In this situation, the front-end treatment member 3 fully retracts into the front end portion of the flexible sheath 1. However, since the front end stopper 6 is fixed at the leading end of the operation wire 2, the flexible friction producing member 4 is not situated on the front side with respect to the front side stopper 6.

Fifth Embodiment

Hereafter, a treatment instrument according to a fifth embodiment is described. Since the fifth embodiment corresponds to a variation of the fourth embodiment, in the following, only the feature of the fifth embodiment is explained. In the drawings for the fifth embodiment, to elements which are substantially the same as those of the fourth embodiment, the same reference numbers are assigned and explanations thereof will not be repeated.

FIG. 10 is a side cross section of the front end portion of the flexible sheath 1 according to the fifth embodiment. In this embodiment, a rear side stopper 7 is additionally provided. The rear side stopper 7 serves to limit the movement of the flexible friction producing member 4 toward the rear side. The rear side stopper 7 is a pipe-like member and is attached to the operation wire 2 on the rear side of the flexible friction producing member 4. For example, the rear side stopper 7 is made of metal or rigid plastic. The rear side stopper 7 has an outer diameter smaller than the inner diameter of the flexible sheath 1 and is fixed to the operation wire 2, for example, by soldering, adhesive joining, or swaging.

FIG. 11 illustrates a situation where the operation wire 2 is fully inserted toward the front side. The length of the operation wire 2 is adjusted such that the front side stopper 6 does not protrude from the front end of the flexible sheath 1 when the operation wire 2 is fully inserted toward the front side. Therefore, the flexible friction producing member 4 is prevented from being detached from the front end of the flexible sheath 1 because even if the flexible friction producing member 4 moves toward the front end of the flexible sheath 1, the movement of the flexible friction producing member 4 toward the front side is stopped by the front side stopper 6.

The movement of the flexible friction producing member 4 toward the rear side is also restricted by the rear side stopper 7 such that the flexible friction producing member 4 is not situated on the rear side with respect to the flexible friction producing member 4.

Figure 12:
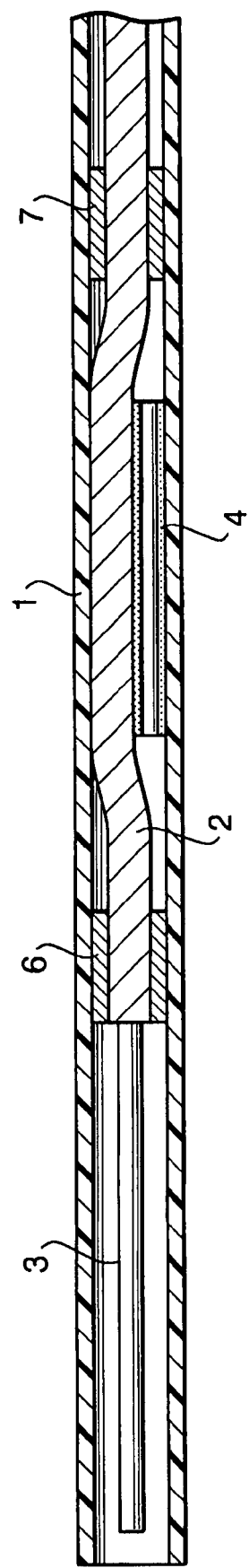
FIG. 12 illustrates a situation where the operation wire is fully withdrawn.

FIG. 12 illustrates a situation where the operation wire 2 is fully withdrawn. In this situation, the front-end treatment member 3 fully retracts into the front end portion of the flexible sheath 1. However, since the front end stopper 6 is fixed at the leading end of the operation wire 2, the flexible friction producing member 4 is not situated on the front side with respect to the front side stopper 6. Since the rear side stopper 7 is provided on the rear side with respect to the flexible friction producing member 4, the flexible friction producing member 4 is not situated on the rear side with respect to the rear side stopper 7.

Sixth Embodiment

Hereafter, a treatment instrument according to a sixth embodiment is described. Since the sixth embodiment corresponds to a variation of the first embodiment, in the following, only the feature of the sixth embodiment is explained. In the drawings for the sixth embodiment, to elements which are substantially the same as those of the first embodiment, the same reference numbers are assigned and explanations thereof will not be repeated.

Figure 13:
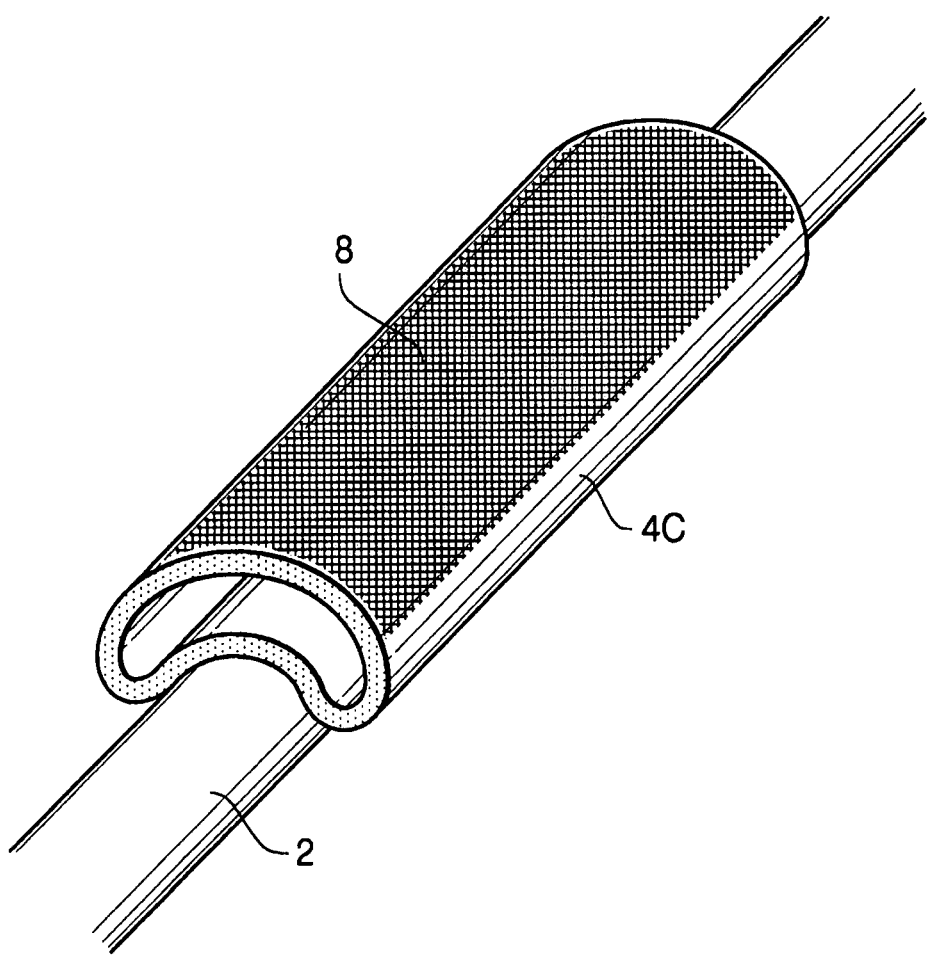
FIG. 13 illustrates an outer appearance of a flexible friction producing member according to a sixth embodiment in the situation where the flexible friction producing member is placed in a flexible sheath.

In this embodiment, a flexible friction producing member 4C is used in place of the flexible friction producing member 4. FIG. 13 illustrates an outer appearance of the flexible friction producing member 4C in the situation where the flexible friction producing member 4C is placed in the flexible sheath 1. In FIG. 13, the flexible sheath 1 is omitted to show the outer appearance of the flexible friction producing member 4C.

As shown in FIG. 13, the flexible friction producing member 4C is subjected to a surface treatment 8 for increasing the friction resistance on the surface not contacting the operation wire 2 (i.e., on the surface contacting the inner surface of the flexible sheath 1). Such a surface treatment 8 can be achieved, for example, by applying a chemical process using a strong acid to the surface of the flexible friction producing member 4C.

Such a configuration enables the flexible friction producing member 4C to reduce tendency to move in the axial direction with respect to the flexible sheath 1. Therefore, according to the sixth embodiment, it is possible to eliminate the need for providing the stoppers 5, 6 and 7.

Seventh Embodiment

Hereafter, a treatment instrument according to a seventh embodiment is described. Since the seventh embodiment corresponds to a variation of the first embodiment, in the following, only the feature of the seventh embodiment is explained. In the drawings for the seventh embodiment, to elements which are substantially the same as those of the first embodiment, the same reference numbers are assigned and explanations thereof will not be repeated.

Figure 14:
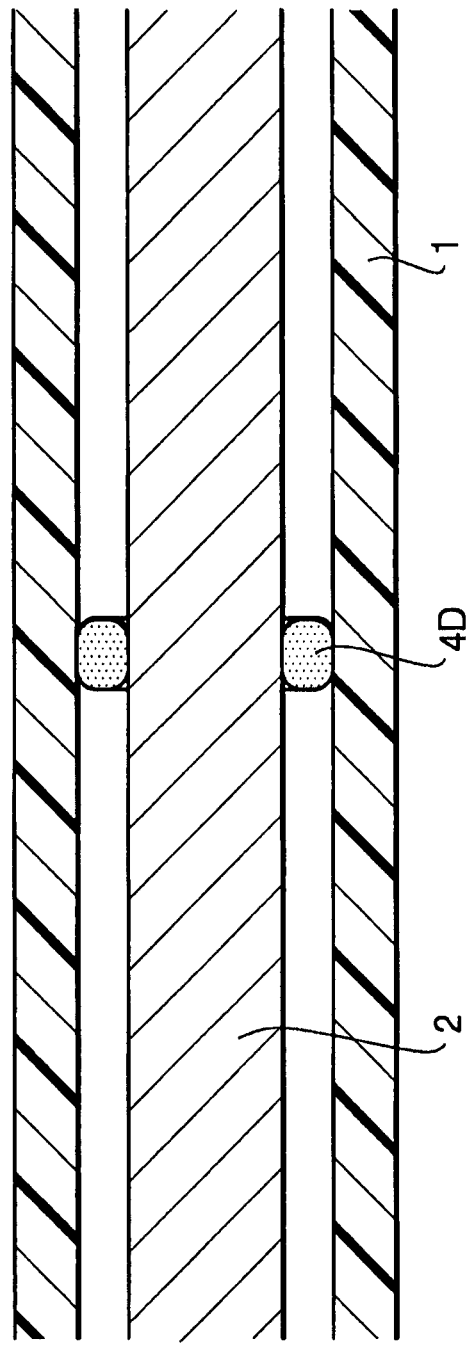
FIG. 14 is a side cross section of a front end portion of a flexible sheath according to a seventh embodiment.

FIG. 14 is a side cross section of the front end portion of the flexible sheath 1 according to the seventh embodiment. In this embodiment, a flexible friction producing member 4D formed of an O-ring made of rubber is provided in the flexible sheath 1 in place of the flexible friction producing member 4.

As described above, a flexible friction producing member for producing friction acting on the movement of the operation wire 2 may be formed of a ring-shaped member having flexibility.

Eighth Embodiment

Hereafter, a treatment instrument according to an eighth embodiment is described. Since the eighth embodiment corresponds to a variation of the first embodiment, in the following, only the feature of the eighth embodiment is explained. In the drawings for the eighth embodiment, to elements which are substantially the same as those of the first embodiment, the same reference numbers are assigned and explanations thereof will not be repeated.

Figure 15:
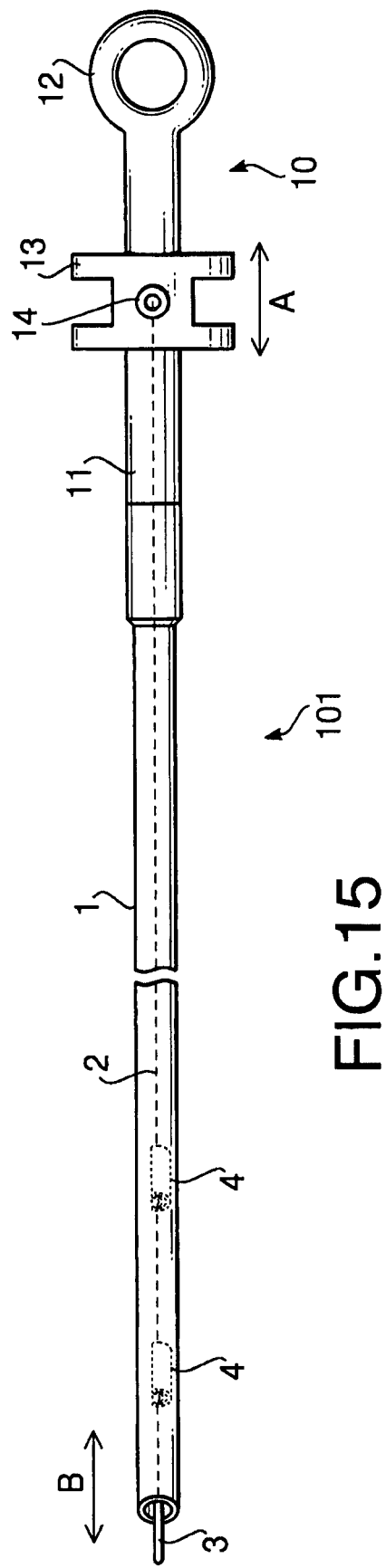
FIG. 15 illustrates the entire configuration of a treatment instrument according to an eighth embodiment.

FIG. 15 illustrates the entire configuration of a treatment instrument 101 according to the eighth embodiment. In this embodiment, two or more flexible friction producing members 4 are provided in the flexible sheath 1 as shown in FIG. 15, for example, by pressing them into the flexible sheath 1. Sizes or materials of the two or more flexible friction producing members 4 may be different from each other.

Ninth Embodiment

As described below, the following embodiments (9$^{th}$ to 14$^{th}$ embodiments) are intended to finely adjust a projected length of a front-end treatment member from a front end of a flexible sheath to a desirable length in a simple manner.

Figure 20:
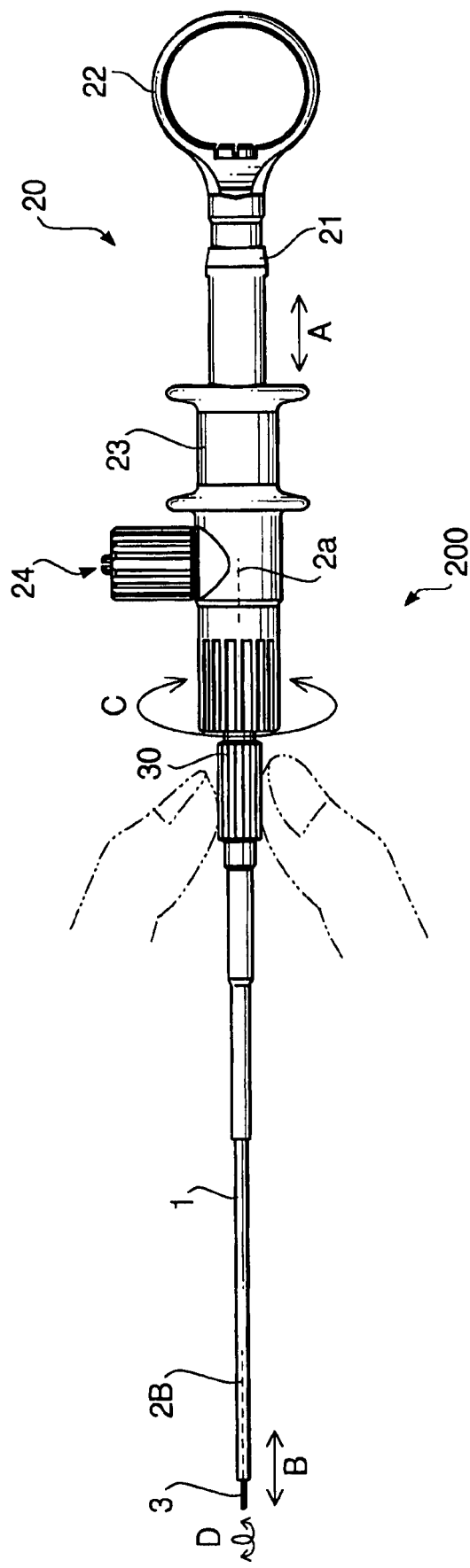
FIG. 20 illustrates the entire configuration of the treatment instrument according to the ninth embodiment.

FIG. 20 illustrates the entire configuration of a treatment instrument 200 for endoscopes according to a ninth embodiment of the invention. In the following drawings, to elements which are substantially the same as those of the first embodiment, the same reference numbers are assigned.

The treatment instrument 200 has a flexible sheath 1 formed of a flexible tube such as a tetrafluoroethylene resin tube, and an operation wire 2B formed of a twisted wire of stainless steel wires having conductivity. The operation wire 2B is elongated in the axial direction along the length of the treatment instrument 200 to be movable in the axial direction. The treatment instrument 200 is inserted into an instrument-inserting channel of an endoscope.

The front-end treatment member 3 is provided at the front end of the flexible sheath 1. The front-end treatment member 3 is a thin straight rod-like member having conductivity to function as a high-frequency electrode. The front-end treatment member 3 is connected integrally with a leading end of the operation wire 2B so that the front-end treatment member 3 is able to protrude from the front end of the flexible sheath 1 and retract into the front end of the flexible sheath 1 in accordance with the movement of the operation wire 2B. The front-end treatment member 3 is also rotatable about the axis line so that it rotates in accordance with rotation of the leading end of the operation wire 2B.

The treatment instrument 200 has an operation unit 20 in which a fixed hook 22 is formed at the rear end of an operation body 21 connected to the proximal end 2a of the operation wire 2B. In the operation unit 20, a movable hook 23 is mounted on the operation body 21 to be slidable along the operation body 21. A terminal 24 is provided on the movable hook 23. When a high frequency power supply cable is connected to the terminal 24, a high frequency voltage is supplied to the front-end treatment member 3 through the operation wire 2B. Consequently, a high frequency treatment can be applied to tissue of a body cavity during a diagnostic operation.

Figure 21:
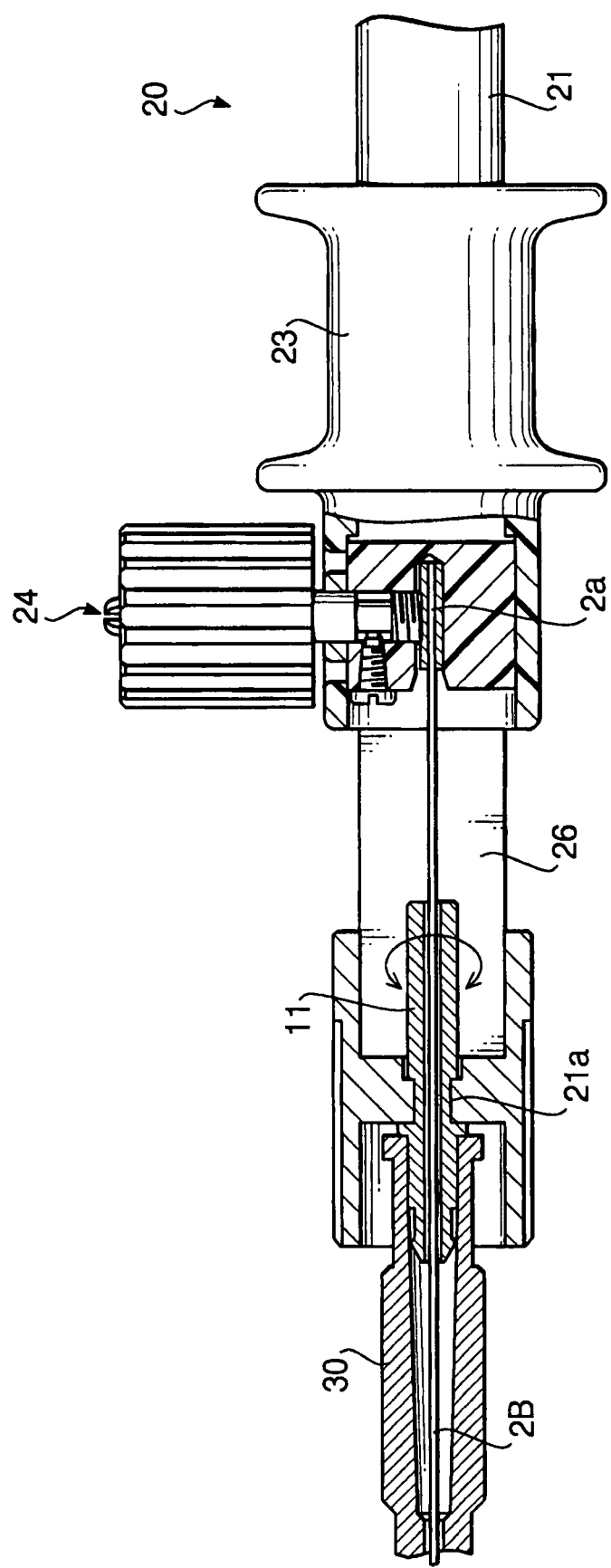
FIG. 21 is a partial side cross section of the treatment instrument according to the ninth embodiment, illustrating an internal structure of an operation unit of the treatment instrument.

An adjustment knob 30 is provided at the proximal end of the flexible sheath 1. FIG. 21 is a partial side cross section of the treatment instrument 200, illustrating the internal structure of the operation unit 20. As shown in FIG. 21, a pin base 11 is coupled to a bearing hole 21a formed in the front end of the operation body 21 so as to be rotatable about the axis line. The adjustment knob 30 is fixed to the front part of the pin base 11. A slit 26 is formed in the operation body 21 so as to slidably catch the movable hook 23 in the axial direction.

By moving the movable hook 23 in the axial direction as shown by an arrow A in FIG. 20, the operation wire 2B moves in the axial direction in the flexible sheath 1 and thereby the front-end treatment member 3 protrudes from the front end of the flexible sheath 1 or retracts into the front end portion of the flexible sheath 1 as shown by an arrow B in FIG. 20. By holding the adjustment knob 30 by fingers as shown in FIG. 20 and rotating the entire part of the operation unit 20 about the axial line, the operation wire 2B rotates about the axis line in the flexible sheath 1 and thereby the front-end treatment member 3 rotates about the axis line at the front end of the flexible sheath 1. As a result, the front-end treatment member 3 moves a small distance in the axial direction. More specifically, the front-end treatment member 3 moves in a spiral fashion.

Figure 16:
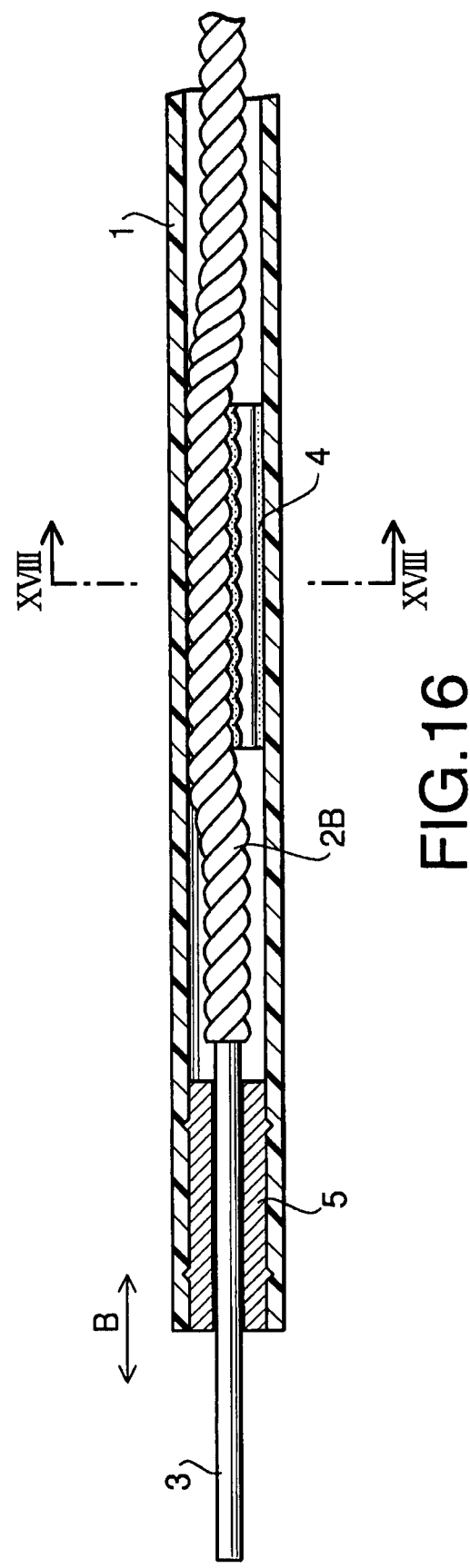
FIG. 16 is a side cross section of a front end portion of a treatment instrument according to a ninth embodiment.
Figure 17:
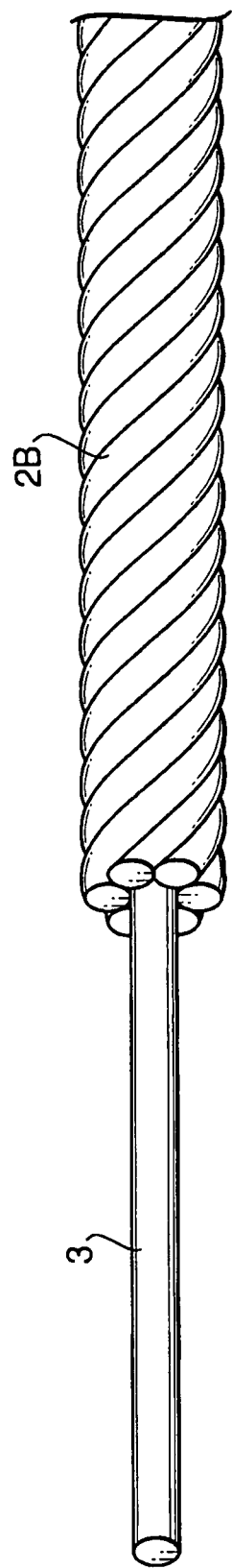
FIG. 17 is a perspective view of a front-end treatment member and an operation wire provided in the treatment instrument shown in FIG. 16.

FIG. 16 is a side cross section of the front end portion of the treatment instrument 200. FIG. 17 is a perspective view of the front-end treatment member 3 and the operation wire 2B. As can be seen from FIG. 17, the front-end treatment member 3 can be formed by elongating one of the twisted wires (e.g., a core wire) forming the operation wire 2B. That is, the front-end treatment member 3 is seamlessly connected to the operation wire 2B.

In this embodiment, the operation wire 2B is formed by twisting seven stainless steel wires (i.e., formed of a so-called 1×7 twisted wire). Alternatively, the operation wire 2B may be formed of a torque wire.

Figure 18:
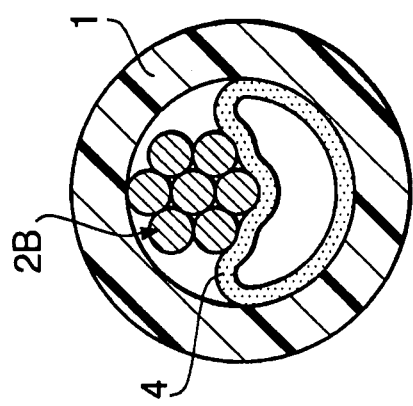
FIG. 18 is a cross sectional view of the treatment instrument along a line XVIII-XVIII in FIG. 16.

FIG. 18 is a cross sectional view of the treatment instrument 200 along a line XVIII-XVIII in FIG. 16. The flexible friction producing member 4 is a flexible tube-like member. As shown in FIG. 16, the flexible friction producing member 4 is pressed into the front end portion of the flexible sheath 1 so that, in a state shown in FIG. 18, the flexible friction producing member 4 is pressed by an outer circumferential surface of the operation wire 2B and an inner surface of the flexible sheath 1 and that the flexible friction producing member 4 has a recessed portion where the flexible friction producing member 4 is elastically deformed by the outer circumferential surface of the operation wire 2B.

Since the flexible friction producing member 4 is simply pressed into the flexible sheath 1, the flexible friction producing member 4 is not fixed with respect to the flexible sheath 1. Such a configuration contributes to reducing the manufacturing cost of the treatment instrument 200.

Figure 19:
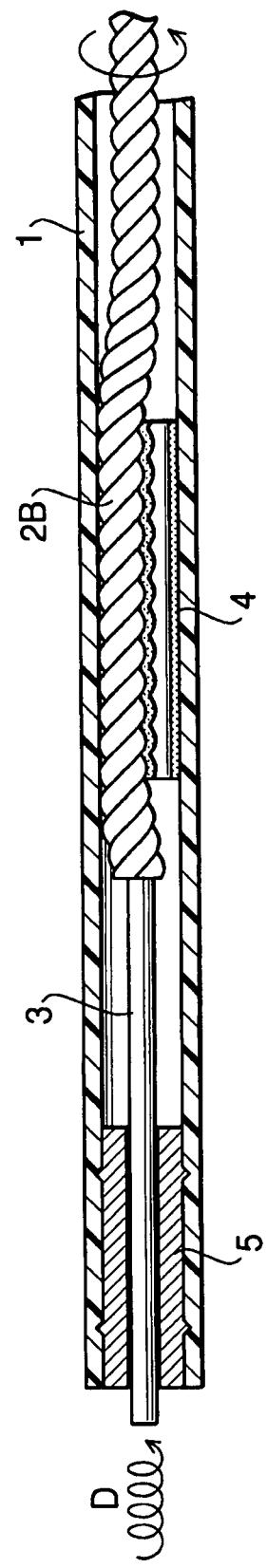
FIG. 19 is a side cross section of a front end portion of a flexible sheath according to the ninth embodiment, illustrating a situation where a front-end treatment member is operated.

In this configuration, by operating the operation unit 20 to rotate the operation wire 2B as shown by an arrow C in FIG. 19, the operation wire 2B rotates about the axis line. In this case, since the flexible friction producing member 4 is pressed against the outer circumferential surface of the operation wire 2B in such a condition that the operation wire 2B engages with the flexible friction producing member 4, the front-end treatment member 3 rotates about the axis line while moving in the axial direction. More specifically, the front-end treatment member 3 moves in a spiral fashion as depicted by arrow D in FIGS. 19 and 20. Consequently, it becomes possible to adjust the projected length of the front-end treatment member 3 from the front end of the flexible sheath 1 in a small amount.

Such a fine adjustment of the projected length of the front-end treatment member 3 is achieved thanks to the engagement of the operation wire 2B to the flexible friction producing member 4 in the condition where the flexible friction producing member 4 is pressed against the operation wire 2B. The fine adjustment is also based on the fact that because a contact surface where the operation wire 2B contacts the flexible friction producing member 4 is smaller than a contact surface where the flexible friction producing member 4 contacts the inner surface of the flexible sheath 1, friction caused between the flexible friction producing member 4 and the flexible sheath 1 is larger than friction caused between the flexible friction producing member 4 and the operation wire 2B.

As described above, according to the embodiment, it is possible to finely adjust the projected length of the front-end treatment member 3 in the situation where the treatment instrument 200 is inserted into an instrument-inserting channel of an endoscope. It should be understood that by simply employing a twisted wire (not having a special configuration for this embodiment) as the operation wire 2B and simply pressing the flexible friction producing member 4 into the flexible sheath 1, the above mentioned advantages of the embodiment can be achieved.

It is also possible to firstly move the movable hook 23 in the axial direction for a rough adjustment of the projected length of the front-end treatment member 3, and secondly rotate the operation unit 20 for a fine adjustment of the projected length of the front-end treatment member 3.

When the operation unit 20 stays in a not operated state, the operation wire 2B is fixed at a position by the friction caused between the operation wire 2B and the flexible friction producing member 4. Therefore, the projected length of the front-end treatment member 3 is not changed by such an external force that is caused when the front-end treatment member 3 touches tissue of a body cavity during a diagnostic operation.

Therefore, it is possible to keep the projected length of the front-end treatment member 3 at a desired length stably.

Similarly to the first embodiment, the stopper 5 is provided at the front end of the flexible sheath 1. The stopper 5 serves to define the maximum projected length of the front-end treatment member 3. The front-end treatment member 3 penetrates the through hole formed in the stopper 5 along the axis line so that the front-end treatment member 3 smoothly moves in the through hole of the stopper 5. The stopper 5 also serves to prevent the flexible friction producing member 4 from being detached from the front-end of the flexible sheath 1.

Similarly to the second embodiment, the flexible sheath 1 may have a narrowed portion at the front end so as to serve as the stopper 5 (see FIG. 4).

Tenth Embodiment

Hereafter, a treatment instrument according to a tenth embodiment is described. Since the tenth embodiment corresponds to a variation of the ninth embodiment, in the following, only the feature of the tenth embodiment is explained. In the drawings for the tenth embodiment, to elements which are substantially the same as those of the ninth embodiment, the same reference numbers are assigned and explanations thereof will not be repeated.

Figure 22:
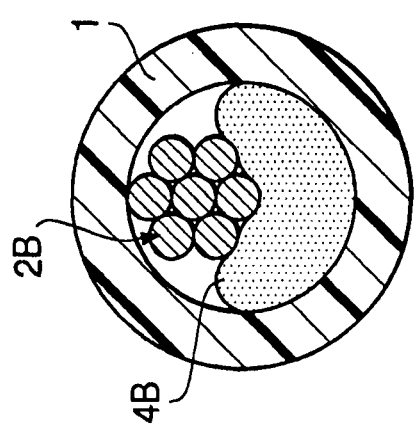
FIG. 22 is a cross section of a front end portion of a flexible sheath according to a tenth embodiment.

FIG. 22 is a cross section of the front end portion of the flexible sheath 1 according to the tenth embodiment. In this embodiment, a solid rod-like member having elasticity (a flexible friction producing member 4B) is used to achieve the same function as that of the flexible friction producing member 4 according to the ninth embodiment. For example, the flexible friction producing member 4B is made of silicon resin or silicon rubber.

Eleventh Embodiment

Hereafter, a treatment instrument according to an eleventh embodiment is described. Since the eleventh embodiment corresponds to a variation of the ninth embodiment, in the following, only the feature of the eleventh embodiment is explained. In the drawings for the eleventh embodiment, to elements which are substantially the same as those of the ninth embodiment, the same reference numbers are assigned and explanations thereof will not be repeated.

Figure 23:
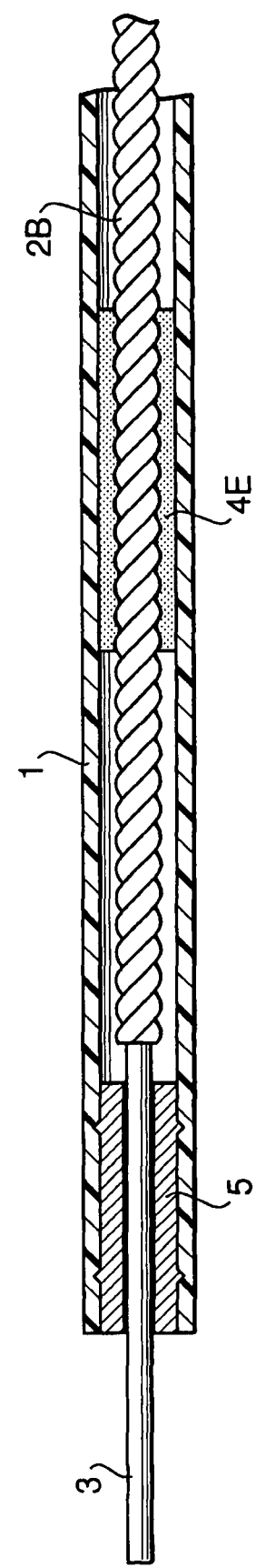
FIG. 23 is a side cross section of a treatment instrument according to an eleventh embodiment, illustrating an internal structure in a front end portion of a flexible sheath.

FIG. 23 is a side cross section of the treatment instrument according to the eleventh embodiment, illustrating the internal structure in the front end portion of the flexible sheath 1. In this embodiment, a flexible friction producing member 4E having a cylindrical shape is used in place of the flexible friction producing member 4. Since the flexible friction producing member 4E has elasticity, the inner surface of the flexible friction producing member 4E elastically deforms when pressed by the outer circumferential surface of the operation wire 2B as shown in FIG. 23.

In this embodiment, the flexible friction producing member 4E is not fixed to the inner surface of the flexible sheath 1. However, the flexible friction producing member 4E may be fixed to the inner surface of the flexible sheath 1. By fixing the flexible friction producing member 4E to the inner surface of the flexible sheath 1, it is possible to prevent the flexible friction producing member 4E from moving together with the operation wire 2B. According to the eleventh embodiment, the same advantages as those achieved by the ninth embodiment can also be achieved.

Twelfth Embodiment

Hereafter, a treatment instrument according to a twelfth embodiment is described. Since the twelfth embodiment corresponds to a variation of the ninth embodiment, in the following, only the feature of the twelfth embodiment is explained. In the drawings for the twelfth embodiment, to elements which are substantially the same as those of the ninth embodiment, the same reference numbers are assigned and explanations thereof will not be repeated.

Figure 24:
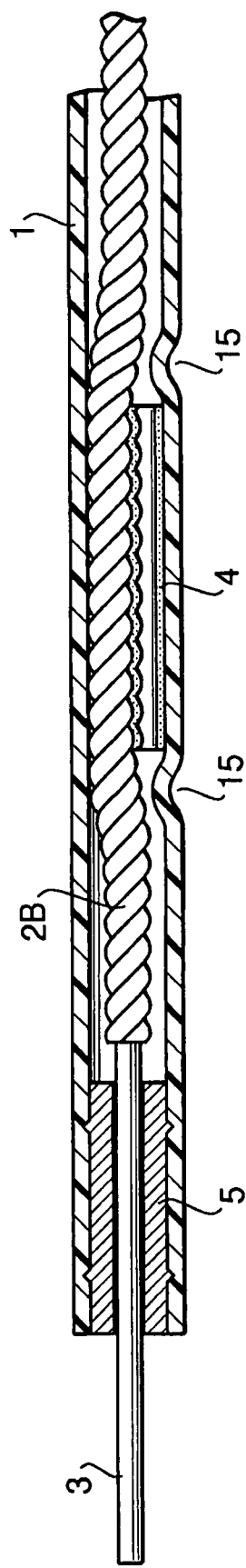
FIG. 24 is a side cross section of a treatment instrument according to a twelfth embodiment, illustrating an internal structure in a front end portion of a flexible sheath.

FIG. 24 is a side cross section of the treatment instrument according to the twelfth embodiment, illustrating the internal structure in the front end portion of the flexible sheath 1. In this embodiment, inwardly-recessed portions 15 and 15 are formed by bending the flexible sheath 1 at certain positions to protrude inwardly. The inwardly-recessed portions 15 and 15 serve to restrict the movement of the flexible friction producing member 4 in the axial direction. According to the twelfth embodiment, the same advantages as those achieved by the ninth embodiment can also be achieved.

Thirteenth Embodiment

Hereafter, a treatment instrument according to a thirteenth embodiment is described. Since the thirteenth embodiment corresponds to a variation of the ninth embodiment, in the following, only the feature of the thirteenth embodiment is explained. In the drawings for the thirteenth embodiment, to elements which are substantially the same as those of the ninth embodiment, the same reference numbers are assigned and explanations thereof will not be repeated.

Figure 25:
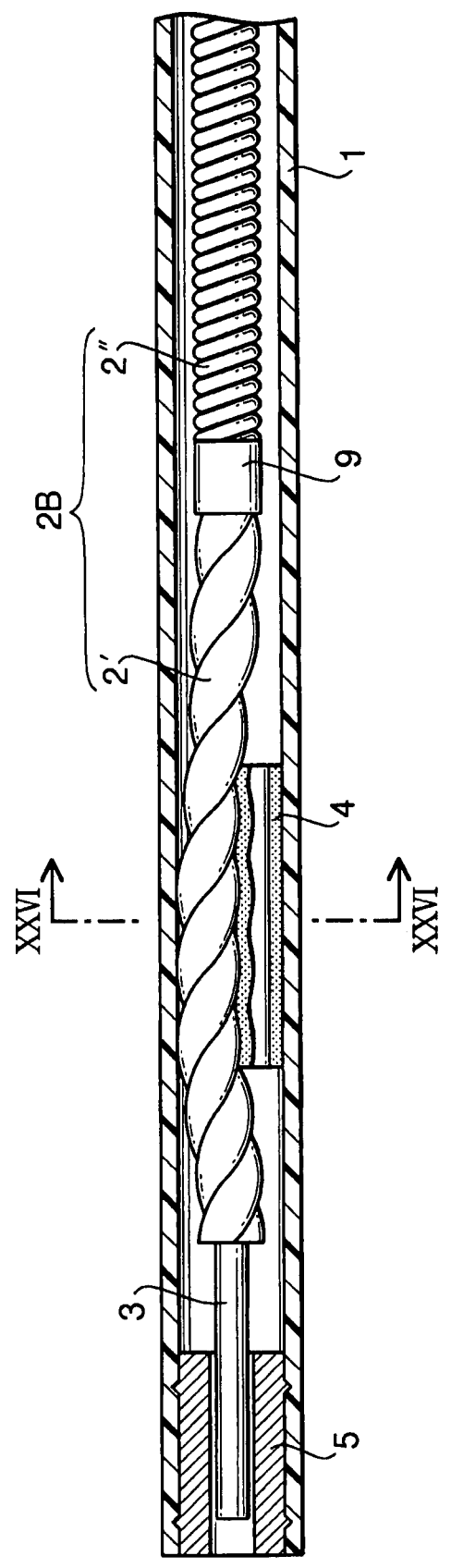
FIG. 25 is a side cross section of a treatment instrument according to a thirteenth embodiment, illustrating an internal structure in a front end portion of a flexible sheath.

FIG. 25 is a side cross section of the treatment instrument according to the thirteenth embodiment, illustrating the internal structure in the front end portion of the flexible sheath 1. In this embodiment, the operation wire 2B includes a first twisted wire part 2' and a second twisted wire part 2" connected with each other in series. The first twisted part 2' is formed at the front end portion where the operation wire 2B is pressed against the flexible friction producing member 4. The first twisted wire part 2' is formed of twisted wires to have a twisting pitch different from that of the second twisted wire part 2". For example, the first twisted wire part 2' may have a larger twisting pitch than the second twisted wire part 2". The first twisted wire part 2' and the second twisted wire part 2" are connected to each other via a connection pipe 9.

Figure 26:
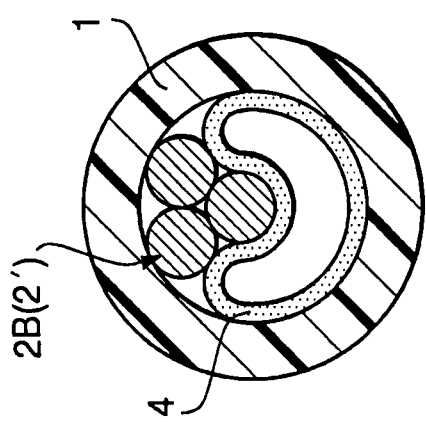
FIG. 26 is a cross sectional view of a treatment instrument along a line XXVI-XXVI in FIG. 25.

FIG. 26 is a cross sectional view of the treatment instrument along a line XXVI-XXVI in FIG. 25. As shown in FIG. 26, the first twisted wire part 2' is formed of three wires (i.e., formed of a so-called 1×3 twisted wire). Each of the wires forming the first twisted wire part 2' has a diameter larger than the diameter of each of wires forming the second twisted wire part 2".

By thus forming the twisted wire 2B, it is possible to increase the moving amount of the front-end treatment member 3 in the axial direction with respect to the rotation angle of the operation wire 2B.

The second twisted wire part 2" may be formed of a torque wire. In this case, it is possible to enhance trackability of the first twisted wire part 2' with respect to the rotational movement of the operation unit 20.

If the entire part of the operation wire 2B is formed of such thick wires as the first twisted wire part 2', the operation wire 2B may have tendency to bend in a certain direction. For this reason, in this embodiment, only the front end portion of the operation wire 2B is formed of relatively thick wires.

Fourteenth Embodiment

Hereafter, a treatment instrument according to a fourteenth embodiment is described. Since the fourteenth embodiment corresponds to a variation of the thirteenth embodiment, in the following, only the feature of the fourteenth embodiment is explained. In the drawings for the fourteenth embodiment, to elements which are substantially the same as those of the thirteenth embodiment, the same reference numbers are assigned and explanations thereof will not be repeated.

Figure 27:
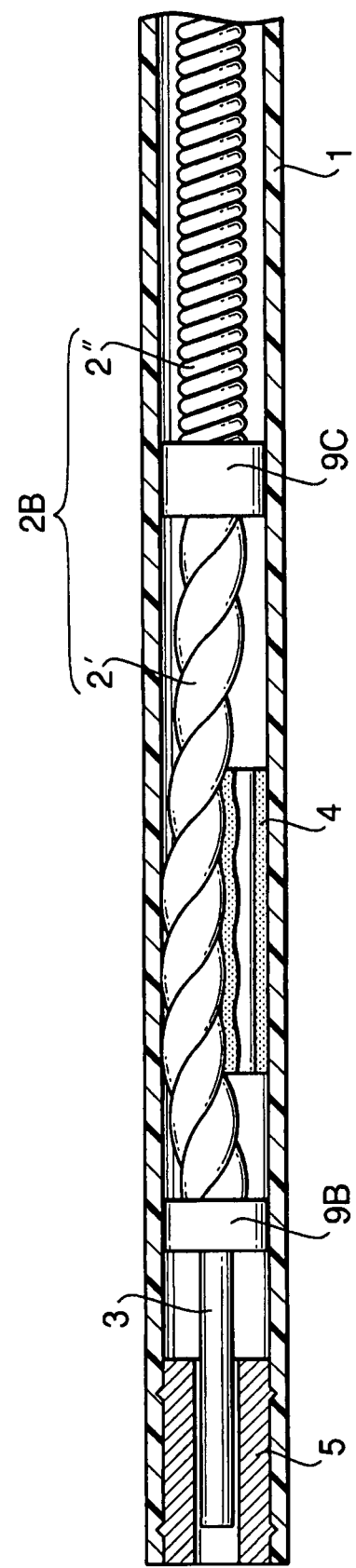
FIG. 27 is a side cross section of a treatment instrument according to a fourteenth embodiment, illustrating an internal structure in a front end portion of a flexible sheath.

FIG. 27 is a side cross section of the treatment instrument according to the fourteenth embodiment, illustrating the internal structure in the front end portion of the flexible sheath 1. In this embodiment, two connection pipes (9B and 9C) are provided at both of the front and rear ends of the first twisted wire part 2'. More specifically, the front end of the first twisted wire part 2' is connected to the front-end treatment member 3 via the connection pipe 9B, and the rear end of the first twisted wire part 2' is connected to the second twisted wire part 2" via the connection pipe 9C.

Although the present invention has been described in considerable detail with reference to certain preferred embodiments thereof, other embodiments are possible.

For example, the shape and size of the flexible friction producing member may be changed in accordance with the intended purpose of the treatment instrument.

The above mentioned configurations of the treatment instrument may be applied to a treatment instrument of the type not applying high frequency current to the front-end treatment member.

This application claims priority of Japanese Patent Applications No. P2006-152950, filed on Jun. 1, 2006, and No. P2006-172259, filed on Jun. 22, 2006. The entire subject matter of the applications is incorporated herein by reference.

What is claimed is:
1. A treatment instrument for endoscopes, comprising:
a flexible sheath configured such that at least a part thereof is formed of a flexible tube;
an operation wire inserted into the flexible sheath to be movable in an axial direction of the flexible sheath;
a front-end treatment member connected to a leading end of the operation wire so that the front-end treatment member is allowed to protrude from a front end of the flexible sheath and retracts into the front end of the flexible sheath in accordance with movement of the operation wire; and
an at least one elastic member that has elasticity and is located in a front end portion of the flexible sheath in a condition where the at least one elastic member is elastically deformed between an inner surface of the flexible sheath and an outer circumferential surface of the operation wire, the at least one elastic member being a tubular member having an outer diameter smaller than an inner diameter of the flexible sheath, the at least one elastic member having a longitudinally extending recess formed on an outer surface of the at least one elastic member,
wherein the operation wire extends along and is positioned within the longitudinally extending recess, and
wherein friction caused among the flexible sheath, the operation wire and the at least one elastic member is applied to movement of the operation wire in the axial direction; and a projected length of the front-end treatment member from the front end of the flexible sheath can be adjusted by moving the operation wire in the axial direction.

2. The treatment instrument according to claim 1, wherein each of the flexible sheath, the operation wire and the at least one elastic member contacts each of the others of the flexible sheath, the operation wire and the at least one elastic member.

3. The treatment instrument according to claim 1, wherein:
the front-end treatment member is a high frequency electrode; and the operation wire has conductivity and is electrically continuous with the front-end treatment member.

4. The treatment instrument according to claim 1, wherein:
the operation wire is formed by twisting a plurality of wires; and
the front-end treatment member is formed by elongating one of the plurality of wires forming the operation wire.

5. The treatment instrument according to claim 1, wherein the at least one elastic member is located in the front end portion of the flexible sheath without being fixed to an inner surface of the flexible sheath.

6. The treatment instrument according to claim 1, further comprising:
a front stopper located in the flexible sheath to prevent the at least one elastic member from being detached from the front end of the flexible sheath.

7. The treatment instrument according to claim 6, wherein the front stopper is located at the front end of the flexible sheath.

8. The treatment instrument according to claim 7, wherein the front stopper is fixed to the front end of the flexible sheath.

9. The treatment instrument according to claim 7, wherein the front stopper is formed by narrowing the front end of the flexible sheath.

10. The treatment instrument according to claim 6, wherein the front stopper is attached to the operation wire.

11. The treatment instrument according to claim 10, wherein the front stopper is a pipe-like member having an outer diameter smaller than an inner diameter of the flexible sheath.

12. The treatment instrument according to claim 10, wherein the front stopper is attached to the operation wire such that the front stopper does not protrude from the front end of the flexible sheath when the operation wire moves to a front end point of a moving range of the operation wire which is allowed to move in the axial direction within the moving range.

13. The treatment instrument according to claim 1, further comprising: a rear stopper located in the flexible sheath to restrict movement of the at least one elastic member toward a rear side.

14. The treatment instrument according to claim 13, wherein the rear stopper is attached to the operation wire.

15. The treatment instrument according to claim 14, wherein the rear stopper is a pipe-like member having an outer diameter smaller than an inner diameter of the flexible sheath.

16. The treatment instrument according to claim 1, wherein the at least one elastic member has an area to which a surface treatment is applied to increase friction caused between the inner surface of the flexible sheath and the area, the area facing the inner surface of the flexible sheath and not facing the outer circumferential surface of the operation wire.

17. The treatment instrument according to claim 1, wherein the at least one elastic member comprises a plurality of elastic members each of which has elasticity and is located in the front end portion of the flexible sheath in the condition where the each of the plurality of elastic members is elastically deformed between the inner surface of the flexible sheath and the outer circumferential surface of the operation wire.

18. The treatment instrument according to claim 1, wherein the at least one elastic member is located in the flexible sheath by pressing the at least one elastic member into the front end portion of the flexible sheath.

19. The treatment instrument according to claim 1, further comprising:
an operation unit that is provided at a proximal end portion of the flexible sheath and is connected to a proximal end of the operation wire so that the operation wire is rotated about an axis line of the operation wire by operating the operation unit,
wherein:
at least a front end portion of the operation wire is a twisted wire formed by twisting a plurality of wires;
the front-end treatment member moves along the axis line when rotated about the axis line by rotation of the operation wire, due to a condition where the front end portion of the operation wire is pressed against the elastic member; and
a projected length of the front-end treatment member from the front end of the flexible sheath can be adjusted by rotating the operation wire using the operation unit.

20. The treatment instrument according to claim 19, wherein an entire part of the operation wire is formed by twisting a plurality of wires.

21. The treatment instrument according to claim 19, wherein:
the operation wire has a first twisted wire part and a second twisted wire part which have twisting pitches different from each other and which are connected with each other in series;
the first twisted wire part is situated at the front end portion of the operation wire to be pressed against the elastic member; and
the second twisted wire part is located on a rear side with respect to the first twisted wire part.

22. The treatment instrument according to claim 21, wherein the twisting pitch of the first twisted wire part is larger than that of the second twisted wire part.

23. The treatment instrument according to claim 21, wherein the second twisted wire part is formed of a torque wire.

24. The treatment instrument according to claim 19, further comprising:
a position restriction member located in the flexible sheath to restrict movement of the elastic member,
wherein the position restriction member prevents the elastic member from moving to a position at which the front end portion of the operation wire does not engage with the elastic member.

25. The treatment instrument according to claim 24, wherein the position restriction member is located at the front end of the flexible sheath.

26. The treatment instrument according to claim 24, wherein the position restriction member is formed by deforming the front end of the flexile sheath.

27. The treatment instrument according to claim 24, wherein:
the position restriction member includes an area which is a part of a surface of the elastic member and has been subjected to a surface treatment; and
the area contacts the inner surface of the flexible sheath and does not contact the outer circumferential surface of the operation wire.

28. The treatment instrument according to claim 24, wherein the position restriction member is attached to the operation wire.

29. The treatment instrument according to claim 19, wherein the operation unit includes:
- a first operation unit configured to rotate the operation wire about the axis line; and
- a second operation unit configured to move the operation wire in the axis direction.

* * * * *